(12) United States Patent
Kreuwel et al.

(10) Patent No.: US 8,187,460 B2
(45) Date of Patent: May 29, 2012

(54) DEVICES FOR SEPARATING, MIXING AND CONCENTRATING MAGNETIC PARTICLES WITH A FLUID

(75) Inventors: Hermannus Johannes Maria Kreuwel, Schijndel (NL); Emiel Gerebern Maria Verwimp, Aaerendonk (BE); Bernardus Jozef Maria Beerling, Heeswijk-Dinther (NL); Franciscus Gerardus Spee, St Michielsgestel (NL)

(73) Assignee: BioMerieux, B.V. (NL)

( * ) Notice: Subject to any disclaimer, the term of this patent is extended or adjusted under 35 U.S.C. 154(b) by 0 days.

(21) Appl. No.: 13/116,333

(22) Filed: May 26, 2011

(65) Prior Publication Data

US 2011/0220567 A1    Sep. 15, 2011

Related U.S. Application Data

(62) Division of application No. 11/572,574, filed as application No. PCT/EP2005/008073 on Jul. 22, 2005, now Pat. No. 7,972,516.

(30) Foreign Application Priority Data

Jul. 26, 2004   (EP) ................................. 04077153

(51) Int. Cl.
  *B03C 1/02*    (2006.01)
  *G01N 1/34*    (2006.01)
  *G01N 1/38*    (2006.01)

(52) U.S. Cl. ........ 210/222; 210/695; 436/526; 422/501; 422/527; 422/547; 422/549; 422/559

(58) Field of Classification Search .................. 210/695, 210/222; 436/526; 422/501, 527, 547, 549, 422/559
See application file for complete search history.

(56) References Cited

U.S. PATENT DOCUMENTS

| 5,705,062 A | 1/1998 | Knobel |
| 6,764,859 B1 | 7/2004 | Kreuwel et al. |
| 7,396,690 B2 | 7/2008 | Colin |

FOREIGN PATENT DOCUMENTS

| EP | 0317286 | 5/1989 |
| EP | 0644425 | 3/1995 |
| WO | WO0105510 | 1/2001 |
| WO | WO03006168 | 1/2003 |

OTHER PUBLICATIONS

International Search Report mailed Oct. 28, 2005 for corresponding PCT application No. PCT/EP2005/008073 (2 pages).
Written Opinion for PCT/EP2005/008073, mailed Jan. 30, 2007.

*Primary Examiner* — David A Reifsnyder
(74) *Attorney, Agent, or Firm* — Myers Bigel Sibley & Sajovec, P.A.

(57) ABSTRACT

The present invention is related to devices for manipulating magnetic particles that are suspended in a fluid, possibly containing a biological entity of interest, the magnetic particles being able to bind the entity of interest, the fluid being contained in a reaction vessel constituted by a large upper compartment with a funnel shape, an elongate lower compartment with a substantially constant cross-section and a closed base. The devices are especially useful in methods for the extraction of nucleic acid to enable them for further processing.

18 Claims, 6 Drawing Sheets

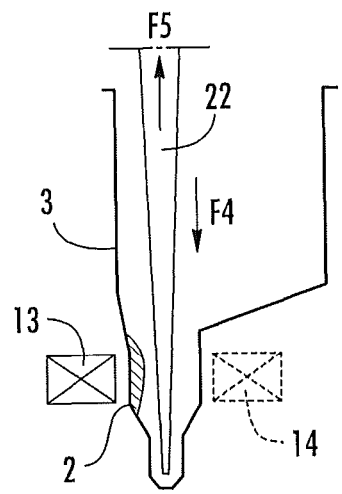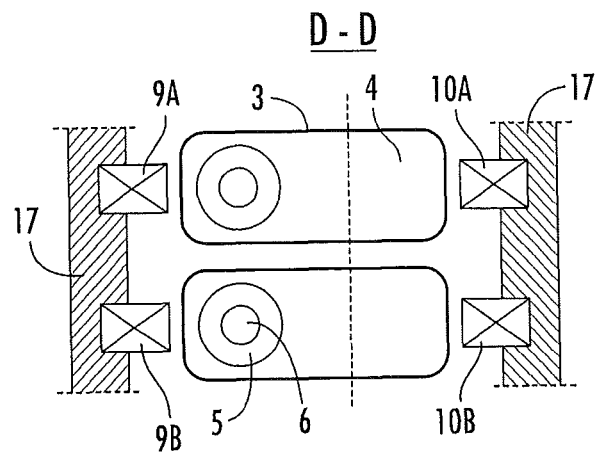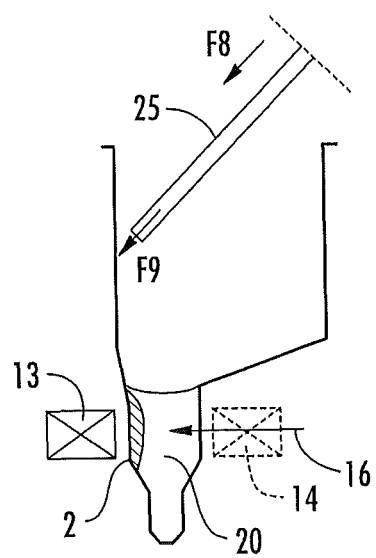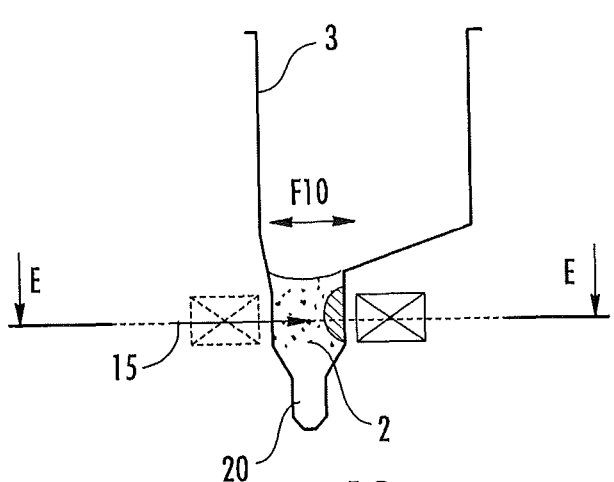

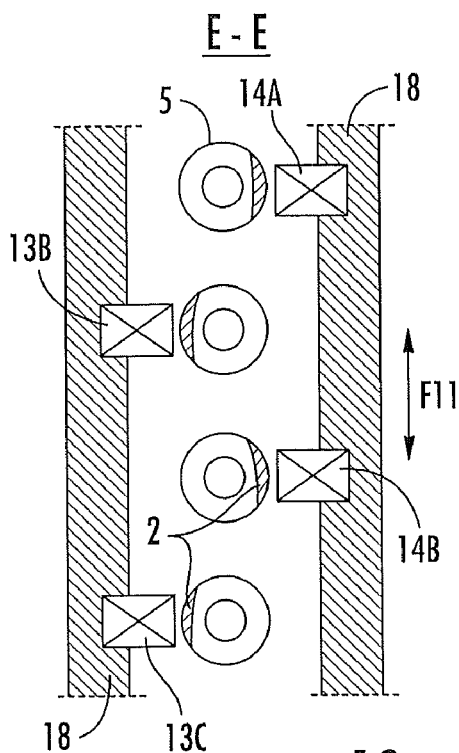
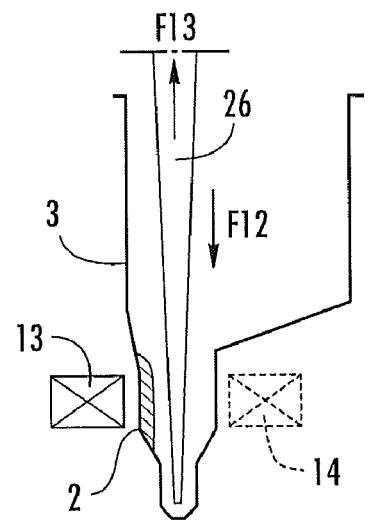
FIG. 13
FIG. 14
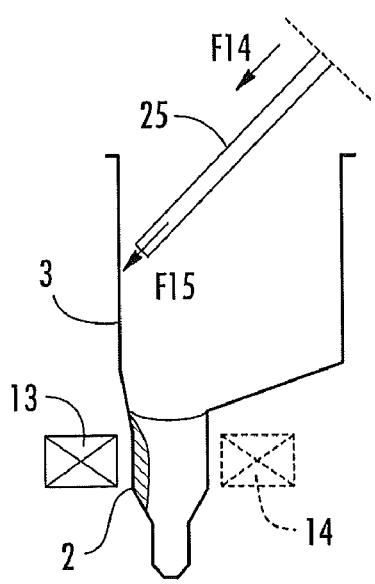
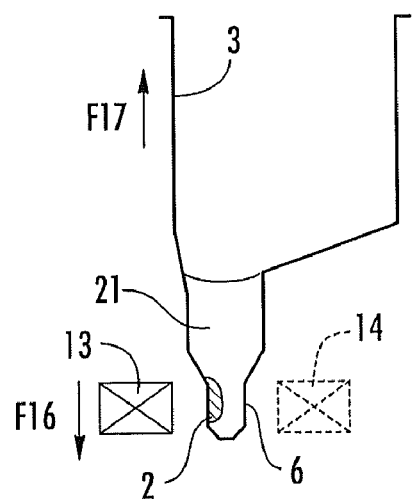
FIG. 15
FIG. 16

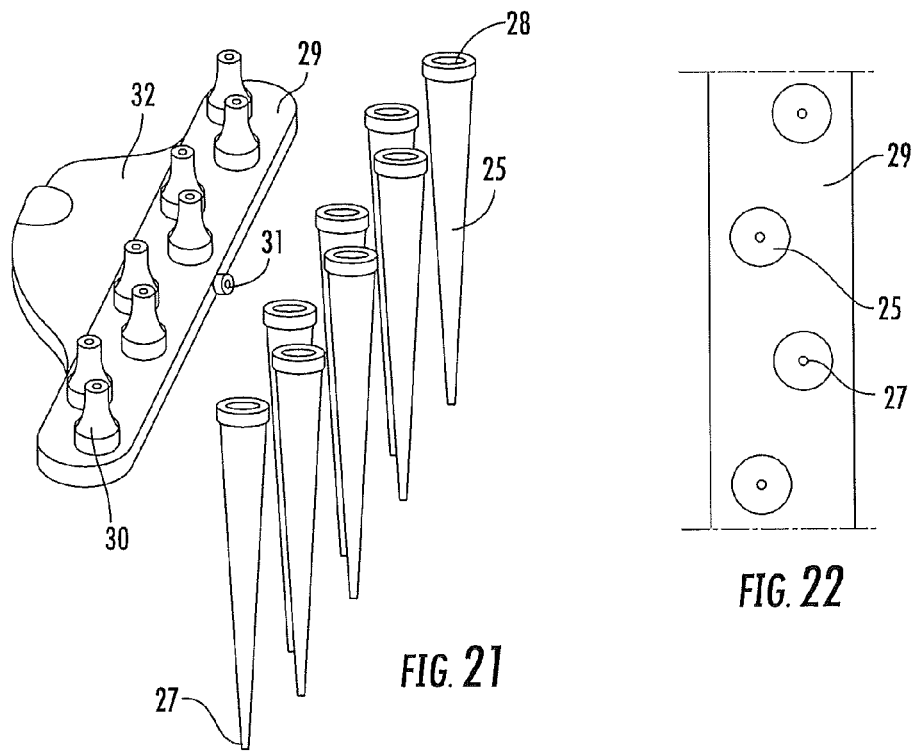
FIG. 21
FIG. 22
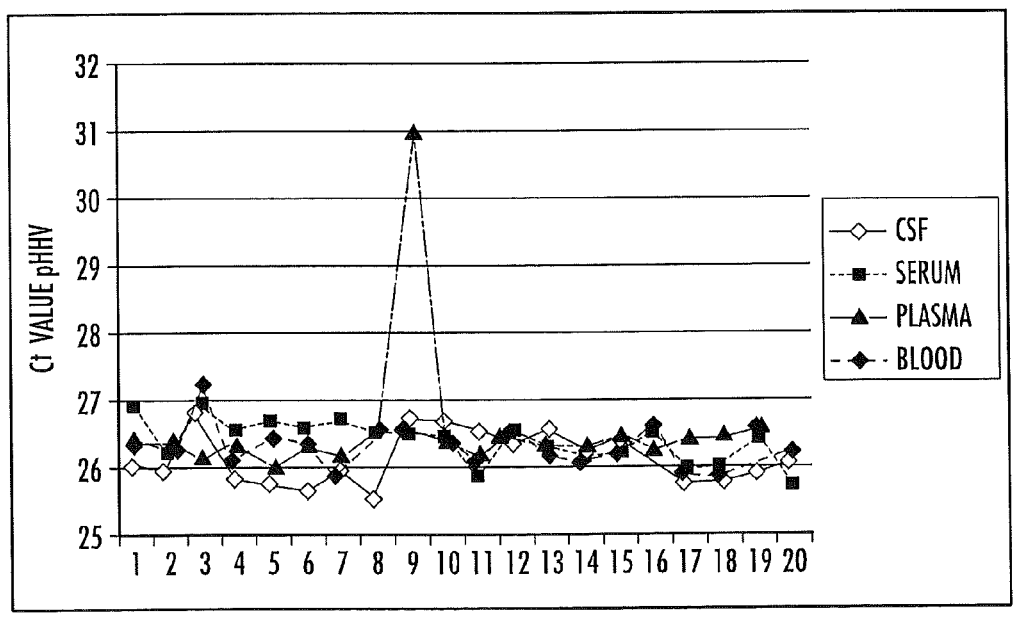
FIG. 23

DEVICES FOR SEPARATING, MIXING AND CONCENTRATING MAGNETIC PARTICLES WITH A FLUID

RELATED APPLICATIONS

This application is a divisional of U.S. patent application Ser. No. 11/572,574, filed Apr. 3, 2007, now U.S. Pat. No. 7,972,516, which is a 35 USC 371 national phase application of PCT/EP2005/008073, filed Jul. 22, 2005, which claims the benefit of European Application Serial No. 04077153.7, filed Jul. 26, 2004, the contents of which are hereby incorporated by reference as if recited in full herein.

FIELD OF THE INVENTION

This invention relates to the use of magnetic or magnetizable particles, and, in particular, to methods of separating, mixing and concentrating magnetic or (super) paramagnetic particles efficiently with a fluid and optionally followed by resuspension of the particles in another fluid. The invention further provided a device for doing the same. In the below-exposed invention, the magnetic particles, paramagnetic particles and superparamagnetic particles will be called magnetic particles.

BACKGROUND

In many methods of biological analysis, a solid phase has to be separated from a liquid phase and subsequently washed. To wash the solid phase, a defined amount of buffer solution is pipetted into the reaction vessel containing the solid phase to suspend the solid phase in the buffer solution. The solid and the liquid phases are then separated. The liquid phase is then removed by suction (aspiration) and a new washing process begins. Usually a number of washing cycles are carried out, each including a suspension, separation and aspiration process.

The use of magnetic particles as a solid phase and separation by permanent magnets is known in principle. Permanent magnets attract the particles to the wall of the reaction vessel and hold them there.

Magnetic particles are often used in separation processes. There are many biological assay methods and purification methods in which magnetic particles are used. For example, immunoassay methods, nucleic acid hybridisation assays and the like. Magnetic particles can also be used in purification methods, to isolate particular components, proteins, nucleic acids, from the material in which they were contained. The particles can be used to separate certain components from a mixture, for example, because they are coated with a reagent with a specific affinity for the component. Magnetic particles can be drawn to, for example, the wall of a container in which the fluid with the magnetic particles was contained and the fluid can be removed and, optionally, be replaced with another fluid. Thus, the particles can be mixed with the fluid from which the specific component is to be removed, the component will bind to the magnetic particle, and a magnet can be used to separate the particles with the component from the remainder of the mixture in the fluid. Optionally the magnetic particles can be washed, and can be separated in another fluid. Or the component can be removed from the particles again into another fluid.

European patent application EP-A-0.136.126 describes a device for separation during solid-phase immunoassays. The bottom end of a reaction vessel containing magnetic particles is disposed between two permanent magnets. The axes of magnetization are at right angles to the wall of the reaction vessel, thus reducing stray magnetic fields:

International application WO-A-92/05443 describes a device for separating magnetic particles. The reaction vessels containing the magnetic particles are disposed in rows. Between the rows is positioned a magnetic block. The reaction vessels are disposed in the magnetic block such that two magnets-are diametrically opposite relative to the reaction vessel. The magnets have alternating polarities and their magnetization axes extend parallel. Separated particles are on only one side of the reaction vessel.

The U.S. Pat. No. 4,895,650, the contents of which is herein incorporated by reference, describes a separating device in which particles are separated by a permanent magnet. The magnet is on only one side of the reaction vessel. The relation between the level of test solution in the test-tube and the position of the magnet is focused on. The position of the magnet, more particularly its height, must coincide with the level of test solution in the reaction vessel, and is brought to the desired height by packing material in the bottom part of the device holding the magnet.

During an immunoassay, the fluid level in the reaction vessels after adding the required reagents is not necessarily uniform. For example, the level in the reaction vessel after adding conjugate solution may be lower than the level after adding washing buffer solution. The method of analysis described in this former U.S. Pat. No. 4,895,650 does not take these differences in level into account.

Known devices for separating magnetic particles have the disadvantage of requiring a relatively long time before all magnetic particles are separated from the liquid phase. Separation time may be considerable, particularly for larger volumes.

A device for rapid separation of magnetic particles is described in European patent application EP-A-0.317.286. In this device, the reaction vessel is surrounded by four permanent magnets (magnets 1, 2, 3 and 4), which are uniformly distributed around a reaction vessel. The direction of the magnetic field of magnets 1 and 3 is rotated through 180° relative to the direction of the magnetic field of magnets 2 and 4. This device has the disadvantage of requiring a relatively large number of permanent magnets to speed up separation. It also excludes many possible cell movements.

In the EP-B-0.644.425 patent is presented an analyser having a device for separating magnetic particles from a suspension, the separation device containing two permanent magnets between which the reaction vessel containing a suspension is located. For faster and more complete separation of the magnetic microparticles, the magnets are located diametrically opposite with respect to the reaction vessel and the pole axes of the magnets form an acute angle with the longitudinal axis of the reaction vessel. An aim of this invention is to provide an analytical device comprising a device for separating magnetic particles such that the magnetic particles in suspension can be rapidly separated even when the reaction vessel is filled to different levels. Another aim is to provide an analytical device for separating magnetic particles such that the magnetic particles in suspension can be separated in a focused manner.

If these documents can be considered for the separation of magnetic particles from a liquid of interest, they cannot authorize a performant mixing that could efficiently wash the particles and give them all chance to bind onto the magnetic particle's surfaces. This efficient step of mixing is absolutely necessary for purifying nucleic acid targets from a biological sample.

State of the Art Concerning the Mixing Step:

Purification methods for nucleic acid using magnetic particles have for example been described in various applications such as EP-A-0.757.106 and WO-A-96/41811. In these applications methods are described wherein a sample solution containing nucleic acids is treated with a chaotropic substance to release the nucleic acid. After releasing the nucleic acids from the biological entity in the lysis buffer, the nucleic acids are bound to the magnetic particles. Both particles coated with a target-specific probe as well as particles having a metal oxide coating (e.g. silica), giving a generic binding of all nucleic acids contained in the sample are used for this purpose. After binding the target, interfering components such as cell debris, enzymes, proteins anti-coagulants and salt are removed by washing the magnetic particles in a (set of) wash buffer(s). Finally, the purified nucleic acids are released from the particles by mixing the particles in a small volume of elution buffer.

For efficient washing and elution the magnetic particles need to be well dispersed and mixed in the relevant buffers. In general, this washing and elution process may be hampered by the aggregation or clogging of the magnetic particles either caused by the adsorption of specific components in the lysed sample (e.g. genomic DNA) or by residual magnetic dipole fields induced in the particles. In particular, the use of silica coated (magnetic) particles with samples that contain significant amounts of genomic DNA (whole blood, sputum, tissue), results in a tight pellet that is difficult to process.

Well-known methods for mixing (magnetic) beads in a liquid buffer are vortexing, sonification or pipetting. These methods however are difficult to automate, and/or give risk of sample to sample contamination by aerosol generation or they may degrade the nucleic acid target. Furthermore, these methods are not well suited for very small volumes of liquid (typically 0.01 ml) as may be required for the elution process.

The method and device according to the invention are especially suitable for use with isolation procedures, where, usually an ingredient is to be isolated in rather pure form from a relatively large volume of sample fluid, and concentrated into a smaller volume of another fluid to be suitable for further use.

In the case of a method for the isolation of nucleic acid such further use may be a nucleic acid amplification method or an assay for the detection of nucleic acid or both.

A method and apparatus for separating and resuspending superparamagnetic particles is disclosed in the application WO-A-91/09308. In this application it was disclosed that superparamagnetic particles may be aggregated and resuspended by subsequent application of different magnetic fields. First and second applications of the magnetic field could be provided with the same magnet, which was then rotated around the container containing the particles to a different location. Two spaced opposed electromagnets, however, could also be used. These electromagnets were energized alternately to produce the first and second magnetic fields that keep the particles in suspension and mix them with the fluid in which they were contained.

A method for the separation of magnetic particles from a fluid is disclosed in U.S. Pat. No. 3,985,649. The particles may be separated from a fluid by bringing the particles into close proximity with a magnet and moved through the liquid along the wall of a container. They may even be moved out of the liquid in this way and can be transported to a second container.

In U.S. Pat. No. 4,988,618, a device is described for use with assays wherein multiple small volume samples are tested at the same time. This type of assay can be performed in, for example, microtiter plates. Magnetic microparticles are present in each well of the microtiter plate. The device thus has multiple orifices and the orifices are each surrounded by multiple permanent magnets, preferably four. The resulting structure of magnets and orifices is rigid; the magnets are not intended to be moved and are mounted in a fixed relation with respect to themselves and to the base of the device. All magnetic are aligned and the field orientation of the magnets may be such that all magnets have the same field direction or neighbouring magnets have opposite field directions. The magnets orientation thus results in four spot attraction sites per orifice. The magnets are purely meant for separation purposes. It is disclosed in the patent that the device may further comprise means or agitating the reagents within the containers.

The applicant has already filed an international application WO-A-0 1/05510 which proposes a solution to improve the mixing. It relates to a method and device, which allows efficient mixing of magnetic or magnetizable particles in a fluid and optionally separation of the particles from said fluid. Use is made of magnetic field of opposite and changing directions. It has been found that, when magnetic or magnetizable particles in a fluid are subjected to these magnetic fields, the particles are, under the influence of the filed, efficiently contacted with the fluid. Such particles normally may tend to form a clot, which can prevent efficient mixing with a fluid. It has been found that, by subjecting the container in which the fluid and the particles are comprised, to magnetic fields of different and changing directions, the particles are efficiently separated from each other and drawn trough the fluid in such a way that a very efficient mixing process occurs. The method allows efficient mixing of particles with even very small fluid volumes. The method of the invention therefore has the advantage that it may save in, for example, washing fluids and may allow the reduction of the volume of fluid needed. Thus, for example in isolation procedures, the method of the invention allows the purification of reagents in high concentrations. Beside, whereas prior art methods can be laborious and time consuming; the method is fast and easy to perform.

Thus, provided with this application is a method of mixing, in one or more container(s), magnetic or (super) paramagnetic particles with a fluid, using more than one magnets, whereby the containers are subjected to magnetic fields with different and changing directions by moving the magnets with respect to the position of the container(s) and/or by moving the containers with respect to the positions of the magnets.

State of the Art Concerning the Concentration Step:

Many diagnostic tests are carried out after steps of extracting the target analytes from biological samples, of purifying in order to remove parasitic products which penalize the performance of the test, of concentrating the target analytes in order to increase the amount of analyte per unit of buffer volume, and of dissolving the target analytes in a buffer in order to make them chemically accessible.

In addition, in order to increase the sensitivity and the specificity of a test for demonstrating an analyte, it is sometimes necessary to reduce the volume of the buffer in which the copies of the analyte being sought are found, while at the same time conserving said analyte in its entirety.

Biologists have entirely conventional means for concentrating an analyte, in particular using centrifugation, filtration and/or magnetic sedimentation techniques. These techniques require transfers of solutions and manipulations of the analyte, which lead to an inevitable decrease in the amount of analyte that can be analysed.

For example, in centrifugation and magnetic sedimentation methods, the actual centrifugation or magnetic sedimentation steps may have to be repeated several times, the limit of the number of repetitions being set by the minimum volume of solution which can be easily and reliably handled with a conventional pipette. This minimum volume is of the order of about 10 micro litres. Below this, transporting it in "large" containers such as pipettes, flasks, etc loses liquid, and therefore analyte. In addition, there are problems of evaporation and of adsorption to the walls of the containers during these manipulations.

In the case of a low concentration of analyte in the starting sample, this may cause the complete disappearance of the analyte or a decrease in the amount thereof such that it may become undetectable.

Besides the abovementioned drawbacks, these manipulations are expensive in terms of material and take a lot of time. This remains a constant problem for many industrial applications, for example the detection of pathogenic micro organisms in a biological specimen or an industrial sample.

The international application, WO-A-02/43865, concerns a method for transporting an analyte present in a sample, a method for concentrating an analyte present in a sample, and a device for implementing said methods. The method for transporting an analyte present in a sample consists in preparing a solution from the sample wherein the analyte is fixed on magnetic particles; introducing this solution in a first container connected via a bottle-neck to a second container; displacing with a magnetic system the analyte fixed on magnetic particles from the first container to the second container via the bottle-neck; the second container being filled with all or part of said solution and/or with another solution.

Here again, the solution is provided to how to concentrate magnetic particles into a small volume of liquid. However the separation is not efficiently treated, especially if the magnet is of a smaller size compared to the first container, and the mixing is even not discussed.

A real need therefore exists for a method and a device for treating analytes bound to magnetic particles while at the same time conserving the amount of analyte present at the start, for example in order to increase the sensitivity and the specificity of diagnostic tests and of any chemical reaction directed towards the analyte, and to overcome the abovementioned drawbacks.

The present invention satisfies this need, and has not only the advantage of overcoming the abovementioned drawbacks, but also many other advantages, which those skilled in the art will not fail to note.

Thus none of the above-described documents presents a process offering the advantages of separating, mixing and concentrating molecules of interest from a liquid sample in only one container. Likewise, they do not propose a container having technical features authorizing the running of such a process. Regardless of the claimed method, it may be either manual or automatic, or operated by an automated device or not.

This is the main goal of the present invention to propose a process for manipulating magnetic particles that are suspended in a fluid, possibly containing a biological entity of interest, the magnetic particles being able to bind the entity of interest, the fluid being contained in a reaction vessel constituted by a large upper compartment with a funnel shape, an elongate lower compartment with a substantially constant cross-section and a closed base, consisting of:

a) subjecting the magnetic particles to two magnetic fields applied simultaneously to separate all said magnetic particles present in at least the upper compartment of the vessel from the fluid,
b) transferring the separated magnetic particles from the upper compartment to the elongated lower compartment,
c) removing the fluid from the vessel,
d) adding a washing liquid to the lower compartment,
e) subjecting the rest of the fluid to at least two magnetic fields applied successively with different and changing directions to wash all the magnetic particles present in the lower compartment, and
f) concentrating said magnetic particles in said lower compartment.

In a particular configuration of the invention, the two magnetic fields applied simultaneously are generated by at least two magnets, the pole axis of the magnets forming together an angle different from 180°, preferably included between 30 and 150° and more preferably included between 60 and 120°.

In another particular configuration of the invention, the at least two magnetic fields applied successively are generated by at least two magnets, the pole axis of the magnets being parallel one to the other.

In a specific embodiment of the latter particular configuration presented just above, the successive magnetic fields with different and changing directions are applied to the vessel by moving the magnets with respect to the position of the vessel and/or by moving the vessel with respect to the position of the magnets.

Always in a particular configuration of the invention, the at least two magnets, cooperating together and having coaxial magnetic fields, and at least two magnets, cooperating together and having magnetic fields that are not coaxial, are positioned on both opposite sides of the vessel.

In a particular configuration of the invention, the magnets are interdependent with one support.

In another particular configuration of the invention, the magnets intended to the separation and the magnets intended to the mixing are identical.

In one embodiment, the support can be moved in rotation around (to pass from separation to mixing configurations) and longitudinally along (to realize the mixing step) an axle passing through each magnet, the axle being parallel to the moving, defined previously, and perpendicularly to magnet's pole axis.

In a particular configuration of the invention, the magnets intended to the separation and the magnets intended to the mixing are different.

According to any of the former particular configurations of the invention, the lower compartment is constituted by:
one medium compartment to which the magnetic fields are applied successively for washing the magnetic particles, and
one bottom compartment in which the magnetic particles are concentrated and to which the magnetic fields are applied successively to bring the particles into contact with the elution buffer.

In one particular configuration, in the main process, above disclosed, between step e) and step f), the following intermediate steps are realized:
e1) transferring the separated and mixed magnetic particles from said medium compartment to said bottom compartment,
e2) removing the washing liquid from the vessel, and
e3) adding an elution buffer to the bottom compartment.

In one particular configuration, in the main process, above disclosed, the following further steps are realized after step f):

g) transferring the magnetic particles from said bottom compartment to the medium compartment or to the upper compartment, h) removing the elution buffer present in the bottom compartment and containing the entity of interest for further processing.

In a preferential configuration, the volume of the medium compartment is smaller compared to the upper compartment and bigger compared to the bottom compartment.

In a particular configuration, the magnet brings about the transfer of magnetic particles.

According to any of the former particular configurations of the invention, the molecules of interest are constituted by nucleic acids (RNA and/or DNA).

On the one hand, the binding of the nucleic acids is non-specific and realized directly onto the surface of the magnetic particles.

On the other hand, the binding of the nucleic acids is specific and realized directly onto capture probes carried by the surface of the magnetic particles.

The present invention also relates to a device for extracting possible molecules of interest from a fluid to which is added a suspension of magnetic or (super) paramagnetic particles contained in at least one reaction vessel and capable to bind the molecules of interest comprising at least one separating station to capture the magnetic particles present in a large upper compartment of each reaction vessel, at least one washing station to mix said magnetic particles present in a medium compartment of each reaction vessel, at least one concentrating station to mix said magnetic particles present in a bottom compartment of each reaction vessel, and at least one pipetting means to dispense and/or to remove part or all of the fluid, the washing liquid and output buffer that are needed to support the process as above presented.

In one embodiment of the device, the separating station comprises at least two magnets, the pole axis of the magnets forming together an angle different from 180°, preferably included between 60 and 150° and more preferably included between 80 and 120°.

In another embodiment of the device, the washing station comprises at least two magnets, the pole axis of the magnets being parallel one to the other.

The invention also relates to a reaction vessel that can be used in an extracting device, above exposed, comprising:

a top aperture,
one upper compartment with a funnel shape,
one medium compartment with a substantially constant cross-section,
one bottom compartment with a substantially constant cross-section,
a closed base, and
a longitudinal axis defined by the lower compartment.

According to one embodiment of the reaction vessel, each of the opposite walls of the upper compartment, constituting the funnel shape, is perpendicular to the pole axis of the magnets that is present with respect to this wall.

According to another embodiment of the reaction vessel, the opposite walls of the upper compartment form together an angle different from 180°, preferably included between 60 and 150° and more preferably included between 80 and 120°.

According to any of the embodiment of the reaction vessel above described, the volume of the medium compartment is smaller compared to the upper compartment (and bigger compared to the bottom compartment.

Again according to any of the embodiment of the reaction vessel above described, the ratio between the volumes of the medium compartment and the upper compartment or between the volumes of the bottom compartment and the medium compartment is comprised between 1:2 to 1:100, preferably between 1:5 to 1:20, and more preferably 1:10.

The invention also relates to a set of reaction vessels constituted by at least two vessels, preferentially at least five vessels and more preferentially eight vessels, according to any of vessels presented above, said vessels being arranged symmetrically along one line.

According to one embodiment of the set of reaction vessels, it cooperates with at least two tips, preferentially at least five tips and more preferentially eight tips, said tips constituting:

a first pipetting mean to dispense and/or to remove part or all of the fluid,
a second pipetting mean to dispense and/or to remove part or all of the wash liquid, and
a third pipetting mean to dispense and/or to remove part or all of output buffer.

According to one embodiment of the set, the free ends of the tips constituting the first or the second or the third pipetting mean being arranged symmetrically along one line or two lines, the two lines of each arrangement being parallel one to the other.

According to another embodiment of the set, the free ends of:

the tips constituting the first pipetting mean being arranged symmetrically along one line,
the tips constituting the second pipetting mean being arranged symmetrically along one or two lines, and
the tips constituting the third pipetting mean being arranged symmetrically along two lines.

According to one embodiment of the set, the first pipetting mean, the second pipetting mean and the third pipetting mean constitute one unique, two or even three different pipetting means.

With "mixing" in this context is meant that the particles and the fluid are brought in close contact. The word "mixing" thus means contacting in a very efficient manner, such as when particles would be washed or reacted with components present in the fluid. Mixing, in this context, does not necessarily provide a homogeneous mixture after the process is finished. The particles may, when the magnets are removed, segregate to the bottom of the container in which they are comprised or may be held to the wall of the container in a particular location by the magnets. The mixing process can for example be used to wash the particles or to react the particles with a component of the liquid, or to bind a component of the liquid to a reagent coated on the particles. Likewise, the mixing process may result in the elution of a certain component originally present on the particles into the surrounding liquid. The method of the invention is applicable in each of these processes and provides an efficient, rapid and convenient way of contacting magnetic or magnetizable particles with a volume of a certain fluid.

The invention will now be described further, by way of examples, with reference to the accompanying drawings, in which:

FIG. 9 is a cross-sectional view of one reaction vessel according to D-D of FIG. 5.

FIG. 10 represents a view, which is similar to FIG. 8, when the vessel is disposed between two other magnets, and after withdrawal of the liquid part of the biological sample.

FIG. 11 represents a view, which is similar to FIG. 10, when the wash liquid is added by way of an oblique tip to avoid splashing.

FIG. 12 represents a view, which is similar to FIG. 11, showing the to and fro movement of the magnetic particles inside the wash liquid.

FIG. 13 is a cross-sectional view of one reaction vessel according to E-E of FIG. 12 explaining the link between the to and fro movement of the magnetic particles and the relative movement of the set of vessels with respect to magnets.

FIG. 14 represents a view, which is similar to FIG. 10, when the vessel is disposed between the same two magnets, but after removal of said wash liquid.

FIG. 15 represents a view, which is similar to FIG. 14 concerning the magnets position, when the output or elution buffer is added by way of the tip, disclosed in FIG. 11, or by way of another tip.

FIG. 16 represents a view, which is quite similar to FIG. 7, when the two other magnets are moved downwardly and transfer the magnetic particles from wash compartment to output compartment.

FIG. 21 is a perspective view of a main body of tips' support separated from eight tips, tips that could be connected to tip supports having a complementary shape.

FIG. 22 is a bottom view of a main body to which the tips have been connected.

Figure 1:
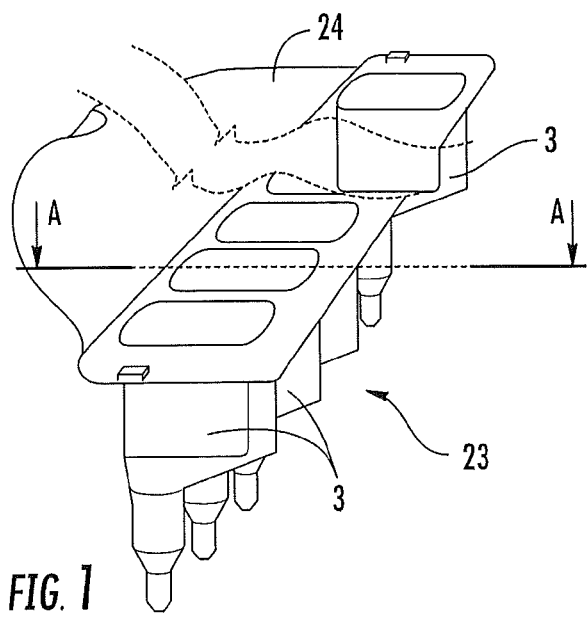
FIG. 1 is a perspective view of a set constituted by eight containers according to the invention.
Figure 3:
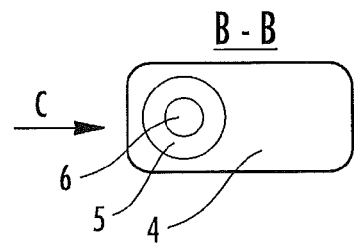
FIG. 3 is a cross-sectional view of the container set according to B-B of FIG. 2.
Figure 2:
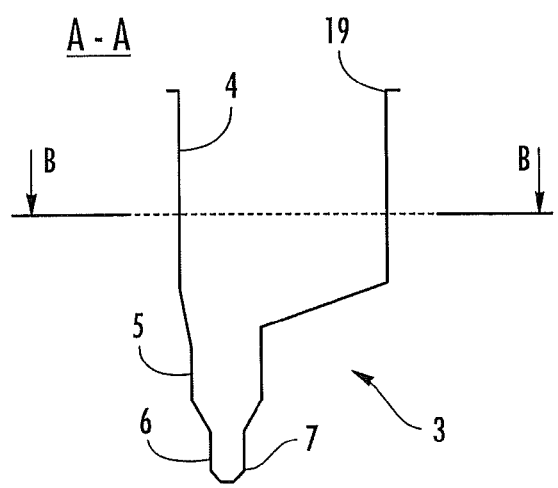
FIG. 2 is a cross-sectional view of the container set according to A-A of FIG. 1.
Figure 4:
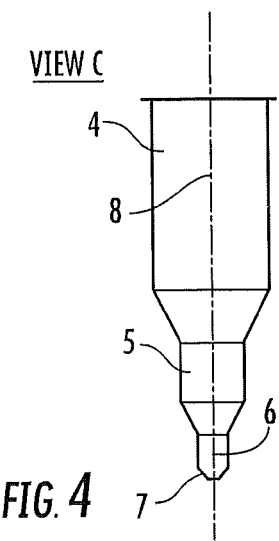
FIG. 4 represents detail C of FIG. 3.

Finally FIG. 23 shows a graphical presentation of the result of a set of real time PCR reactions where a DNA fragment of the Porcine herpesvirus (PhHV-I) has been amplified after isolating the virus from different samples using the device disclosed in this patent application. Along the horizontal axis different sample numbers are indicated. The vertical axis shows the threshold cycle for each sample when a positive PCR signal is observed. Four different sample types have been used (CSF, plasma, serum and blood). With each sample type 20 individual samples have been used.

1—DESCRIPTION OF THE PREFERRED EMBODIMENT

1.1—Details of the Reaction Vessel

The vessel 3 is well disclosed on FIGS. 1-4. It consists in three compartments:
a large upper incubation compartment 4 with a funnel shape of the vessel 3,
an elongated medium wash compartment 5 with a constant cross-section of the vessel 3
an elongated bottom output compartment 6 with a constant cross-section of the vessel 3
This configuration obliges to have a top aperture 19 where it is possible to introduce/dispense or remove any liquid present inside said vessel 3, but also a closed base 7. Finally, according to FIG. 4, the vessel 3 has a longitudinal axis 8.

Now referring more particularly to FIG. 1, vessels 3 in a preferential configuration are arranged to constitute a set 23, having a manipulation tongue 24 that facilitates the handling by the users. Positioning means not represented on the Figures, could be added in order to render the installation in an automatic device even more efficient than usual.

The main features are:
Preferably, the total height of the vessel 3 is 40 mm to facilitate recovery of the output buffer 21 from the output compartment 6 using a standard disposable filter tip, like 22, 25, 26.
Volume of incubation compartment 4 is 2-6 ml, preferably 4 ml. In the later configuration, which is the current design, the dimensions are 20 mm in high, 25 mm in depth, 9 mm in width.
Volume of wash compartment 5 is 0.1-1 ml, preferably 0.2 ml. In the later configuration, which is the current design, the cylindrical shape has 5 mm as diameter and 8 mm as height.
Volume of output compartment 6 is 10-100 µl, preferably 20 µl. In the later configuration, which is the current design, the cylinder is 5 mm in height and 2 mm in diameter.
The thickness of the wall of the vessel is between 0.2 mm and 1 mm (current design: 0.5 mm).

Preferably, the reaction vessel is a plastic disposable produced by injection moulding for example using polypropylene. To allow convenient manipulation by an operator, it is recommended to integrate several reaction vessels 3 into a set 23. The applicant has realized a design where a set comprises eight vessels 3. For the same reason it is convenient to integrate the tips 21, 25, 26 with their common base 29 to obtain a single unit where the number of tips equals the number of reaction vessels 3 and where the spacing between tips matches with the position of vessels in a set 23.

Preferably the device uses magnets fabricated from neodymium (NdFeB) with a remnant field of 1.2 Tesla. With the current device, cylindrical magnets of 6 mm diameter and 7 mm length have shown suitable for the magnets 9, 10 13 and 14.

Figure 18:
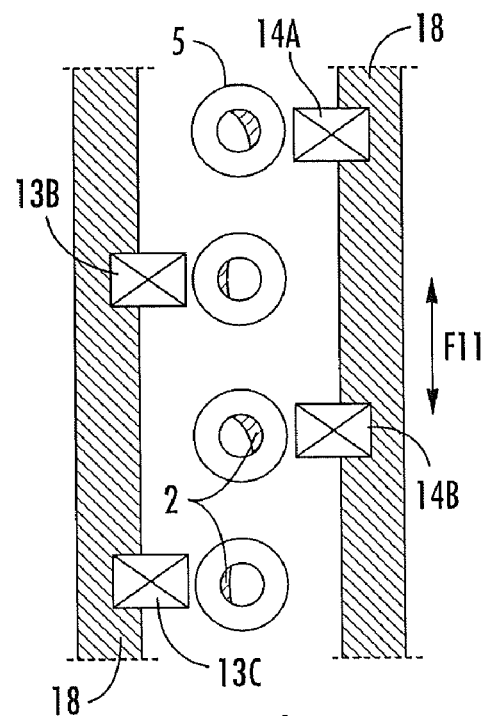
FIG. 18 represents a view, which is similar to FIG. 13, explaining the to and fro movement of the magnetic particles in the output buffer due to the relative movement of the set of vessels with respect to the magnets.

When separating magnetic particles 2 from the liquid 1 in the incubation compartment 4, the spacing between the face of the magnets 9 and 10 and the wall of the reaction vessel is typically 0.5 mm. During the wash movement (FI1, FIG. 13) the magnets 13 and 14 are translated with respect to the vessel with a typical velocity of 1 cm per second. When passing the vessel, the distance to the wall of the wash compartment 5 is typically 1 mm. During the elution movement (FI1, FIG. 18) the magnets 13 and 14 are translated with respect to the vessel with a typical velocity of 1 cm per second. When passing the vessel, the distance to the wall of the output compartment 6 is typically 2 mm.

1.2—Method According to the Invention

In a preferred embodiment, the device disclosed in this application is combined with some standard components such as a suction pump and liquid line for aspirating liquid, a liquid dispenser module and some mechanical means for translating the magnets, the aspiration tip and the dispenser with respect to the reaction vessels. In a preferred embodiment, this device is useful for isolating nucleic acids from a complex starting biological sample, such as whole blood, blood serum, buffy coat (the crusta phlogistica or leukocyte fraction of blood), urine, feces, liquor cerebrospinalis, sperm, saliva, tissues, cell cultures and the like. Nucleic acid as isolated from above-mentioned biological material can also comprise the endogenous nucleic acid from the organism from which the sample is derived and any foreign (viral, fungal, bacterial or parasitic) nucleic acid.

The device is used according to the following procedure:

(a) Add Liquid Mixture to the Reaction Vessel

A mixture 1 of the primary sample, a lysis buffer and magnetic particles 2 is added to the reaction vessel 3. The target molecules (nucleic acid, not shown on the Figures) are released from the cells or organisms in the sample and bind to the magnetic particles 2. This process step is defined as "incubation". In this step, all the compartments, constituting said vessel 3, are filled up with the fluid 1, i.e. incubation compartment 4, wash compartment 5 and output compartment 6. Due to the difference in size in between said compartments 4-6, most of said fluid 1 is contained in the incubation compartment 4 of the reaction vessel 3. Typically, the incubation time is about 5 minutes.

(b) Separate Particles from the Sample

Figure 5:
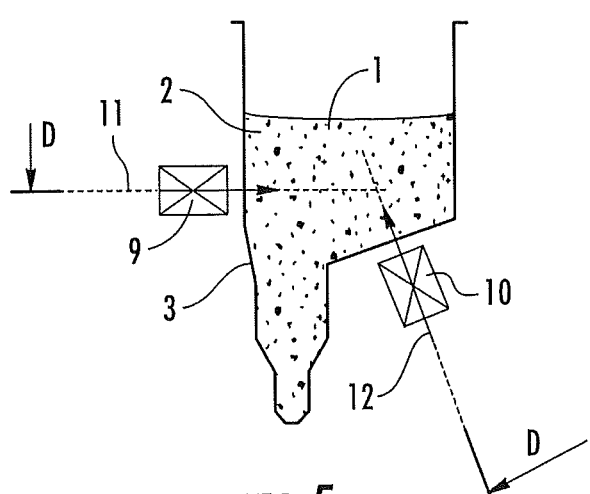
FIG. 5 represents a view, which is similar to FIG. 2, in the case the vessel filled up with the biological sample is disposed between two magnets, acting simultaneously on the fluid.
Figure 6:
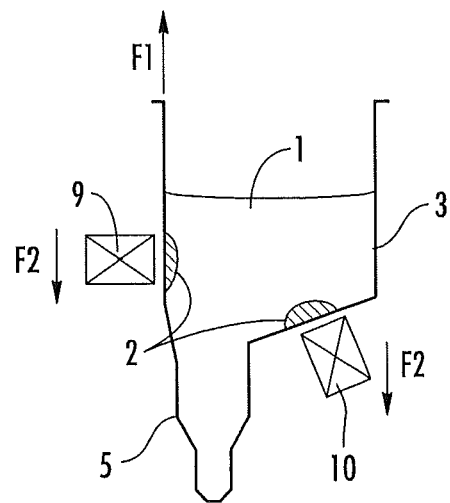
FIG. 6 represents a view, which is identical to FIG. 5, after the two magnets have attracted all magnetic particles present in the starting sample.

After incubation, the liquid mixture 1 in the vessel 3 is disposed between two magnets 9A or 9B or 9C, etc. and respectively 10A or 10B or 10C, etc.; each one 9 or 10 generating a magnetic field respectively 11 and 12, as disclosed in FIG. 5. The configuration is also well defined in FIG. 9. As a result, the magnetic particles 2 are collected—as a pellet—at two positions at the sidewall of the incubation compartment 4 corresponding to the location of the magnets (FIG. 6). Collection time is typically around 1 minute.

(c) Transfer Particles to Wash Compartment

Figure 7:
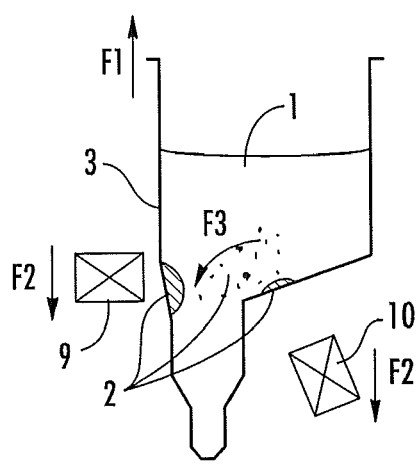
FIG. 7 represents a view, which is similar to FIG. 6, when said two magnets are moved in downward direction and transfer the magnetic particles from incubation compartment to wash compartment.
Figure 8:
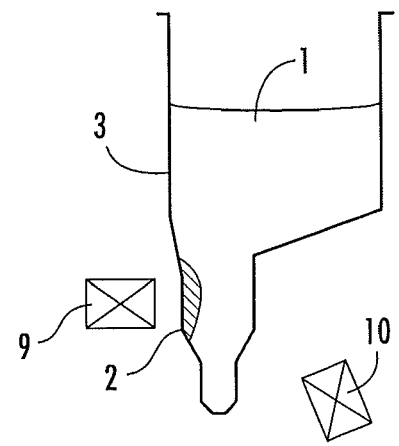
FIG. 8 represents a view, which is similar to FIG. 7, when the magnets have reached their final position and all magnetic particles have formed a single pellet.

According to FIG. 7, the pellets of magnetic particles 2 are transferred from the incubation compartment 4 to the wash compartment 5 by moving the magnets 9 and 10 in the downward direction according to F2. It is also possible to achieve this movement by moving the vessel 3 in the upward direction according to F1, or to combine the down (F2) and upward (F1) movements of respectively said magnets 9 and 10 and said vessel 3. During that movement(s), the particles 2 initially collected by magnet 10, jump over towards magnet 9, according to F3, where they join with the particles 2 initially collected by magnet 9. After this consolidation, all magnetic particles 2 are transferred to the wash compartment 5 as shown in FIG. 8.

(d) Wash Magnetic Particles

The magnetic particles 2 are washed to remove all sample components as well as other ^reagents that could interfere with the downstream application. Washing is achieved by disposing the reaction vessel 3 to the magnets 13 and 14 and subsequent removal (F5) of the liquid sample from the reaction vessel 3 using the tip 22 (FIG. 10), which is introduced vertically, according to F4, in said vessel 3. Next, according to FIG. 11, a fresh wash liquid 20 is added into said vessel 3 according to F9 by mean of a tip 25 introduced in the vessel according to F8, which is at an oblique angle compared to the vertical position of the vessel 3 in order to eliminate any risk of splashes that could generate drops on the internal sidewall, prejudicial to further future process steps. During sample removal and liquid addition, the magnetic particles 2 are retained at the sidewall of the wash compartment 5 under the action of the magnets 13 and 14. Next, the magnets 13 and 14 are moved in the direction FI1, as depicted on FIG. 13, to transfer the particles 2 back and forth, according to F1O of FIG. 12, between opposite sides of the wash compartment 5 to bring them in contact with the wash liquid 20. In those circumstances, magnetic particles 2 are alternatively submitted to two opposite magnetic fields 15 and 16.

Obviously it is also possible to achieve this movement in the F11 direction by moving the vessel 3 with respect to the magnets 13 and 14, or to combine movements of both said magnets 13 and 14 and said vessel 3.

Step (d) can be repeated until sufficient wash performance has been obtained. If appropriate a sequence of different wash liquids can be used. In case different wash liquids are used it will be clear that the dispense tip is washed adequately when changing buffers.

The magnets 13 and 14 are placed in intervening array geometries. This layout allows the use of the method of the invention to give a high throughput format. An embodiment wherein the vessels and the magnets are placed in intervening array geometries is illustrated in FIG. 13. The vessels 3 are placed in array geometry with the magnets 13A, 13B, 13C, etc., on one side and 14A, 14B, 14C, etc., on the other side, fixed to a second array 18, used as a support for the magnets, that translates with respect to the vessels 3.

In this way a large series of samples is processed simultaneously. Addition and aspiration of liquids may be by hand or by an automated multi-tip dispenser instrument as know in the art. Such a configuration is well exposed by the Applicant in a former application filed under application number WO-A-0 1/05510 published the 25 Jan. 2001 and entitled: "Device and method for mixing magnetic particles with a fluid and optionally separating the particles from the fluid and use thereof in purification methods". Readers could find relevant information about said configuration in this document. This is the reason why its content is enclosed for reference.

(e) Prepare for Elution

Figure 17:
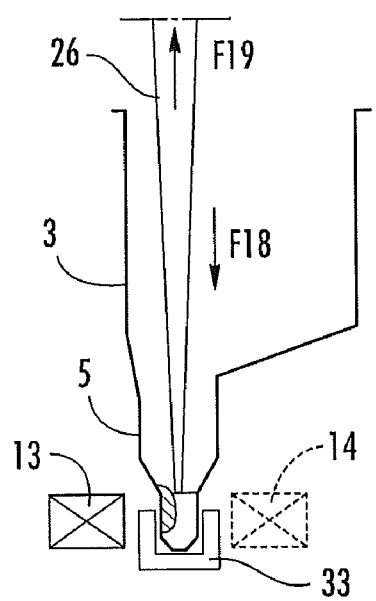
FIG. 17 represents a view, which is similar to FIG. 16, after removal of output buffer present in the wash compartment. At this stage, the output buffer is submitted to a heating system in order to achieve elution of molecule of interest.

While the magnetic particles 2 are retained at the sidewall of the wash compartment 5, all wash liquid is removed from the vessel 3, according to F13, using tip 26 that is introduced in the vessel 3 according to F12, to end up in the configuration as depicted in FIG. 14. Next, an output or elution buffer 21 is added by way of tip 26 or a new tip, not represented on the drawing, introduced according to F14, to the reaction vessel 3 to fill (F15) the output—and the wash compartments 6 and 5. After that, the magnetic particles 2 are transferred from the wash compartment 5 to the output compartment 6 by moving the magnets 13 and 14 in the downward direction (F16) and/or by moving the vessels 3 in the upward direction (F17) (FIG. 16). Next, the volume of output buffer 21 is set by descending tip 26 into the reaction vessel 3, according to F18, while aspirating part of the liquid, according to F19, to a level that corresponds with the specified volume of output buffer (FIG. 17).

Figure 19:
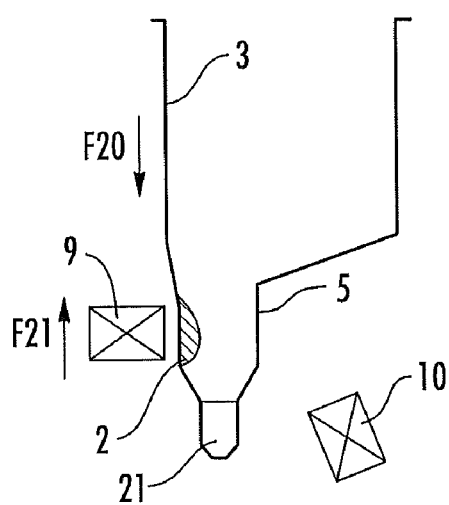
FIG. 19 represents a view, which is quite similar to FIG. 16, but using the two former magnets to move upwardly and transfer the magnetic particles from output compartment to wash compartment where no liquid is present.

Although the magnetic particles 2 are in contact with the elution buffer 21 no significant release of target takes place due to the fact that:
   the contact time is short,
   said magnetic particles 2 are collected as a clump, and
   the elution buffer 21 is at room temperature.
   (f) Heat the Elution Buffer A heater element 33 is enclosing the output compartment 6 of the reaction vessel 3 to heat the output buffer to a specified temperature (FIG. 17). A typical temperature for the elution process is 60-80° C. This temperature is applied during about 15 seconds to 10 minutes, preferably 1 minute to 6 minutes and more preferably 3 minutes. These conditions authorize significant release of target.
   (g) Elute Nucleic Acid from Magnetic Particles The target molecules are released from the magnetic particles 2 and recovered in the output buffer 21, only present in the bottom compartment 6, by moving the magnets 13 and 14 in the direction FI1, according to FIG. 18. Similar to the washing step (d), the particles 2 are translated back and forth between opposite sides of the output compartment 6 to bring said particles 2 in efficient contact with the output buffer 21. During this step the heater 33 is enclosing the output compartment 6 to control the temperature of the output buffer 21.
   (h) Separate Magnetic Particles from Output Buffer After the elution step, the magnetic particles 2 are cleared (separated) from the output buffer 21 by disposing the sample vessel 3 to the magnets 9 and 10, see FIG. 19, to allow magnet 9 to collect the particles 2 at the sidewall of the output compartment 6 and subsequently move the vessel 3 in the downward direction, according to F20, and/or move the magnets 9 and 10 in the upward direction, according to F21, in order to maintain said particles 2 at the sidewall of the incubation compartment 4, as disclosed in FIG. 20, or optionally of the wash compartment 5.

Figure 20:
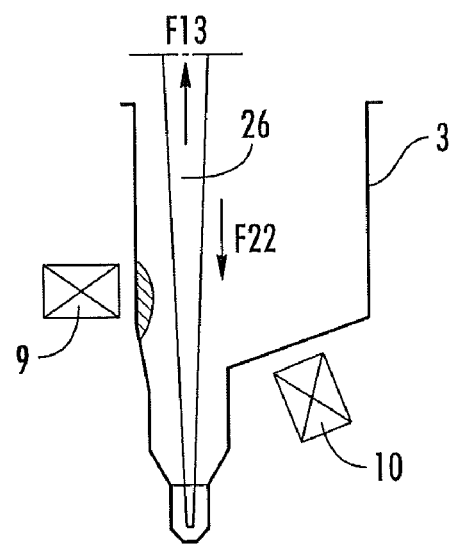
FIG. 20 represents a view, which is quite similar to FIG. 19, where the upward movement is maintained so that the magnets transfer the magnetic particles from wash compartment to incubation compartment to authorize the removal of the rest of output buffer containing the eluted molecules of interest from the output compartment.

Then the elution buffer 21 present in the output compartment 6 could be used for further processing or, according to FIG. 20, be transferred by mean of tip 26, which is introduced (F22) into the vessel 3 and the elution buffer 21, containing the target molecules, is removed by aspiration (F23).

It will be clear to anybody skilled in the art that the device disclosed above as well as the method for using the device is easily integrated in an automated system by performing the translations for the reaction vessel, the magnets, the heater and the tips in an automated way, for example using a set of linear actuators controlled by stepper motors. It is also obvious that, depending on the particular application, particular steps of the above protocol can be omitted such as (f), (g) or Qx).

FIGS. 10 and 14 are quite similar, as the magnetic particles 2 are maintained in position in a single vessel by a only one magnet 13, for instance. Each neighbouring vessel 3 of the set 23 contains also magnetic particles 2 that are attracted by magnet 14. In other words, neighbouring vessels 3 have their magnetic particles 2 on opposite sidewalls. To facilitate the introduction of tips 22 or 25 in the eight vessel's set 23, the positioning of said eight tips has been implemented in an improved manner, as disclosed in FIGS. 21 and 22. Thus all the tips that collaborate with one set 23 of vessels 3 are associated with a main body 29, this latter having eight tip supports 30, each 30 shifted one to the other. More specifically each tip comprises two free ends, one is the lower end 27 and the other one is the upper end 28 of the tip. The free ends 27 or 28 are arranged symmetrically along two lines, each line being drawn by four lower end 27 or four upper end 28, and the two lines being parallel one to the other.

Obviously when the tips 22 or 25 are introduced in the vessels 3, according to FIGS. 10 and 14, the tips are taken away as much as possible from the magnetic particles 2, to avoid any contact prejudicial to further future process steps.

Now referring more particularly to FIG. 21, main body 29 in a preferential configuration comprises a manipulation tongue 32 that facilitates the handling by the users. Positioning means not specifically represented on the Figures, could be added in order to render the installation in an automatic device even more efficient than usual. Moreover, said main body 29 comprises an admission/exhaust aperture 31 to permit the dispensing or the removing of any fluid. This aperture 31 could also serve as positioning means.

Four examples are presented where nucleic acids are isolated from an input sample using the invention presented above. With these examples the wash buffers, the elution buffer and the magnetic particles were obtained from the "*NucliSens magnetic extraction reagents*" (article code 200297). The lysis buffer is the "*NucliSens Lysis buffer*" (article code 200295). NucliSens products are supplied by bioMérieux B. V. (Boxtel, The Netherlands)

2—EXAMPLE 1

Concentration of Ribosomal RNA from Plasma Samples 2.1—Materials and Methods

Target RNA is extracted from *Escherichia coli* cells using the Qiagen RNA/DNA maxi kit (article code 14162, Qiagen, Hilden, Germany). For each sample, 2 micrograms (µg) are used as input.

Sample is constituted by normal EDTA/citrate plasma samples from a pool of 100 individual blood donations.

The RNA quantification is performed using a luminescent marker for RNA (Sybr Green-II, supplied by Molecular Probes: article S-7564) in combination with a luminescent-reader for microtiter plates ("Victor$^2$", supplier Wallac Oy, Turku, Finland: 1-420-multilabel counter).

Purity of the output buffer is determined from the relative value for the spectral absorption at 260 nm and 280 nm (A260/A280) using an UV spectrophotometer (supplier Unicam, Cambridge, Great Britain: Unicam UV-I).

2.2—Sample Preparation

A set of twenty-four plasma samples is prepared as follows:
   With each sample, 1 ml of plasma is added to the reaction vessel and mixed with 2 ml NucliSens Lysis buffer.
   Next, the target rRNA is added to that mixture using an input of 2 µg RNA for each sample.
   Subsequently, 1 mg of magnetic particles is added to the lysed plasma samples and a homogeneous dispersion is produced using a manual pipette.

2.3—Extraction Method

A batch of twenty-four samples is processed simultaneously according to the procedure indicated above as steps (a) to (g). The samples are added to three sets of reaction vessels, each set comprising eight identical vessels.

After collecting the magnetic particles from the incubation compartment (collection time was 1 minute), the particles are transferred to the wash compartment and washed using NucliSens wash buffer 1 and wash buffer 2, using two cycles of 3 ml and 1 ml in the first and second cycle respectively.

After washing, the particles are transferred to the output compartment where the target RNA is released from the particles by mixing the particles in the NucliSens elution buffer (wash buffer 3) for 5 minutes. During elution, the temperature of the buffer is 60° C. The volume of the output buffer is 20 µl.

After elution, the magnetic particles are separated from the output buffer using the magnets 9.

After completing the protocol, the amount of RNA recovered in the output compartment of each vessel is measured using a luminescent RNA marker. For that purpose, 10 µl of the output buffer is transferred from each reaction vessel into the well of a microtiter plate and 190 µl of Sybr Green solution is added to each well. In each well, the optical signal detected by the luminescent plate reader (Victor$^2$ is a direct measure for the amount of RNA that is present in that well.

2.4—Result

For the twenty-four samples, the average amount of target rRNA in the output compartment of the vessel is 1.32 µg with a standard deviation of 50 ng. This corresponds to an average yield of 66%.

Purity of the output is excellent as concluded from the A260/A280 ratio using the UV spectrophotometer. The output buffer shows a ratio of 2.1 whereas pure RNA in this buffer has an A260/A280 ratio between 1.9 and 2.1.

Consistency of the target RNA is determined using the 2100 Bioanalyzer (Agilent Technologies, Amstelveen, Netherlands). This instrument detects the two discrete RNA bands corresponding to the 16S and 23S RNA. No other products such as smaller RNA fragments have been detected.

The total time for completing the extraction procedure for this batch of twenty-four samples is 30 minutes, starting after adding the magnetic particles to the lysed samples. No intervention from an operator is needed to produce the concentrated RNA in the output.

3—EXAMPLE 2

Concentration of Plasmid DNA from Plasma Samples

3.1—Materials and Methods

Target is a plasmid DNA, pBR322 (article N3033L, New England Biolabs Inc., Beverly, Mass.), linearized by BamH1 (article E1O1OWH, Amersham Bioscience Corp, NY, USA). Six µg of DNA is used as input per sample The sample is constituted by 0.1 ml normal EDTA/citrate plasma from blood donations

3.2—Sample Preparation

Twenty-four samples are processed simultaneously, using the same procedure as with example 1. The individual plasma samples are added to the reaction vessels. Next, 2 ml of NucliSens lysis buffer are added. Subsequently, the plasmid DNA is spiked to the sample and 1 mg of magnetic particles is added to the mixture.

3.3—Extraction Method

The collection step, washing steps and elution step of the extraction procedure are identical to example 1.

3.4—Result

After completing the procedure, the amount of extracted DNA is determined from the optical density of the output buffer at 260 nm.

The average amount of DNA recovered from the reaction vessel is S.1 µg with a variation coefficient of 4% between different vessels. This corresponds to an isolation yield of 52% using 6 µg of DNA as input.

The average A260/A280 ratio for the output buffer is 1.9. For pure DNA in the output buffer this ratio is between 1.7 and 2.1.

As with example 1, the time needed to complete the extraction procedure is 30 minutes starting after adding the magnetic particles.

4—EXAMPLE 3

Recovery of Viral RNA from Sputum Samples

4.1—Materials and Methods

In this experiment, the recovery of HIV RNA that is spiked to nine sputum samples is determined using the NucliSens EasyQ HIV-I assay version 1.1 (article 285029, bioMerieux B.V., Boxtel, The Netherlands).

The RNA is HIV RNA obtained from a cultured HIV-I type B virus stock (HXB2) that is lysed using the NucliSens lysis buffer and calibrated against the WHO International HIV-I RNA standard.

The sputum samples were obtained from the University Hospital of Antwerpen (Belgium).

4.2—Sample Preparation

With each sputum sample a volume of 1 ml is mixed with 0.5 ml of protease solution (100 mg/ml) and incubated on a plate shaker for 20 minutes at room temperature to obtain a liquefied sample.

The target HIV RNA is spiked to a tube containing 2 ml of NucliSens lysis buffer, using 30.000 copies input for each sample. Together with the HIV RNA, a calibrator RNA that is part of the EasyQ kit is added to the lysis buffer. Next the liquefied sputum samples are added to the reaction vessel together with the lysis buffer (2 ml) containing the RNA. After 10 minutes, 1 mg of magnetic particles is added to each sample. A homogeneous dispersion is obtained by mixing with a manual pipette.

4.3—RNA Extraction

The extraction procedure proceeds as with the examples 1 and 2 described above.

4.4—RNA Detection

At the end of the extraction procedure, the HIV RNA and calibrator RNA are concentrated in 12 µl of elution buffer in the output compartment. Two fractions of 5 µl each are aspirated from the output compartment and used as input in a NucliSens EasyQ assay. For the detection, the procedure as indicated in the EasyQ assay manual is followed.

4.5—Result

The results are presented in the table here below:

| Sample number | EasyQ result (viral copies) | |
|---|---|---|
| | Reaction 1 | Reaction 2 |
| 1 | 11.000 | 10.000 |
| 2 | 11.000 | 9.700 |
| 3 | 9.600 | 9.200 |
| 4 | 12.000 | 13.000 |
| 5 | 11.000 | 16.000 |
| 6 | 18.000 | 13.000 |
| 7 | 9.200 | 10.000 |
| 8 | 12.000 | 14.000 |
| 9 | 20.000 | 12.000 |

From these results, we conclude that the device disclosed in this application is well able to isolate viral RNA from sputum samples and concentrate it in a form that facilitates detection using standard amplification methods.

5—EXPERIMENT 4

Recovery of Viral DNA from Different Sample Types

5.1—Materials and Methods

This experiment represents a series of four extraction runs on twenty-two samples each. With each run a different sample type is used:

Run 1: plasma samples from individual donations (1 ml per sample)

Run 2: Cerebra Spinal Fluid (CSF) (0.1 ml per sample)

Run 3: serum samples from individual donations using 1 ml per sample

Run 4: whole blood samples (0.1 ml per sample).

5.2—Sample Preparation

Each sample is added to 2 ml NucliSens lysis buffer.

As a target, the Porcine herpesvirus (PhV-I) is spiked to twenty of the lysed samples in each run. Two samples ($21^{st}$ and $22^{nd}$) were used as a negative control (no DNA spiked).

5.3—DNA Extraction

The extraction method for each run (sample type) is identical to the procedure described in the examples I, 2 and 3.

5.4—DNA Detection

The DNA that is recovered in the output buffer is detected using a real time PCR. The number of PCR cycles (CT) needed to produce a positive signal is determined for each sample.

The FIG. 23 shows a graphical presentation of these CT values for all samples. The negative control samples were all negative.

5.5—Result

From this set of experiments, we conclude that the device disclosed in this patent application is well able to isolate nucleic acid from virus particles from different sample types with excellent yield.

REFERENCES

1. Fluid or mixture
2. Magnetic particles
3. Reaction vessel
4. Large upper incubation compartment with a funnel shape of the vessel 3
5. Elongate medium wash compartment with a constant cross-section of the vessel 3
6. Elongate bottom output compartment with a constant cross-section of the vessel 3
7. Closed base of the vessel 3
8. Longitudinal axis of the vessel 3
9. Magnets (A, B, C, D, etc.) present on one side of the container set used for the separation step
10. Magnets (A, B, C, D, etc.) present on the other side of the container set used for the separation step
11. Pole axis (A, B, C, D, etc.) of the magnet (9A, 9B, 9C, 9D, etc.)
12. Pole axis (A, B, C, D, etc.) of the magnet (10A, 10B, 10C, $10D_5$ etc.)
13. Magnets (A, B, etc.) present on one side of the container set used for the mixing and/or the concentrating step(s)
14. Magnets (A, B, etc.) present on the other side of the container set used for the mixing and/or the concentrating step(s)
15. Pole axis (A, B, etc.) of the magnet (13A, 13B, 13C, 13D, etc.)
16. Pole axis (A, B, etc.) of the magnet (14A, 14B, 14C, 14D, etc.)
17. Support of the magnets (9A, 9B, 9C, 9D, etc., or 10A, 10B, 10C, 10D, etc.)
18. Support of the magnets (13A, 13B, 13C, 13D, etc., or 14A, 14B, 14C, 14D, etc.)
19. Top aperture of the vessel 3
20. Wash liquid
21. Output buffer
22. Tip for adding or removing fluid 1
23. Set of vessels 3
24. Manipulation tongue of vessels' set 23
25. Tip for adding wash liquid 20 and/or elution buffer 21
26. Tip for removing wash liquid 20 and/or output buffer 21
27. Lower end of tip 25
28. Upper end of tip 25
29. Main body of tips' support 30
30. Tip support
31. Admission/exhaust aperture of the main body 29
32. Manipulation tongue of main body 29
33. Heating system
F1. Upward movement of vessel 3
F2. Downward movement of magnets 9 and 10
F3. Magnetic attraction of particles 2
F4. Downward movement of tip 22
F5. Removing of fluid 1 by aspiration with tip 22
F8. Downward movement of tip 25

F9. Dispensing wash liquid 20 expulsed from tip 25
F10. Movement to and fro of magnetic particles 2
F11. Relative movement of the set 23 with respect to magnets 13 and 14
F12. Downward movement of tip 25
F13. Removing of wash liquid 20 by aspiration with tip 25
F14. Downward movement of tip 26
F15. Dispensing output buffer 21 expulsed from tip 26
F16. Downward movement of magnets 13 and 14
F17. Upward movement of vessel 3
F18. Downward movement of tip 26
F19. Removing output buffer 21 present in wash compartment 5
F20. Downward movement of vessel 3
F21. Upward movement of the magnets 13 and 14
F22. Downward movement of tip 26
F23. Removing of output buffer 21 by aspiration with tip 26

That which is claimed:

1. An apparatus for extracting possible molecules of interest from a fluid, comprising:
   a plurality of aligned one reaction vessels adapted to receive a fluid and a suspension of at least one of magnetic or paramagnetic particles capable to bind molecules of interest, each reaction vessel comprising an upper compartment with a funnel shape that merges into an elongate middle compartment, then into a closed base, wherein the elongate middle compartment of the at least one reaction vessel has a longitudinally extending centerline that is offset from a longitudinally extending centerline of the upper compartment, wherein the upper compartment has a substantially vertically extending sidewall that is substantially aligned with a sidewall of the elongate middle compartment and an opposing substantially vertically extending sidewall that resides above and merges into a floor portion that is inclined to define the funnel shape so that the floor portion directs the fluid toward a channel associated with the elongate middle compartment;
   at least one separating station to capture the magnetic and/or paramagnetic particles present in the large upper compartment of each reaction vessel characterized in that the at least one separating station comprises at least two magnets, each pole axis of the magnets intersecting in the reaction vessel at an angle different from 180° and are directed to apply magnetic fields substantially concurrently to the upper compartment;
   at least one washing station to mix the magnetic and/or paramagnetic particles present in the middle compartment of each reaction vessel characterized in that the at least one washing station comprises at last two magnets, a pole axis of the magnets are in-line or parallel one to the other; and
   at least one concentrating station to mix the magnetic and/or paramagnetic particles present in the base compartment of each reaction vessel.

2. Device for extracting possible molecules of interest from a fluid, comprising:
   at least one reaction vessel comprising the fluid and a suspension of at least one of magnetic or paramagnetic particles capable to bind the molecules of interest, each reaction vessel having a large upper compartment with a funnel shape, an elongate middle compartment and a closed bottom compartment;
   at least one separating station to capture the magnetic and/or paramagnetic particles present in the large upper compartment of each reaction vessel, wherein the at least one separating station comprises at least two magnets, a pole axis of the magnets forming together an angle different from 180°,
   at least one washing station to mix said magnetic and/or paramagnetic particles present in the middle compartment of each reaction vessel, wherein the at least one washing station comprises at last two magnets, a pole axis of the magnets being in-line or parallel one to the other,
   at least one concentrating station to mix said magnetic and/or paramagnetic particles present in the bottom compartment of each reaction vessel, and
   at least one pipetting device that cooperates with a respective reaction vessel to dispense and/or to remove part or all of the fluid, a washing liquid and an output buffer used in an extraction process.

3. Device according to claim 2, wherein the at least one reaction vessel is a plurality of aligned reaction vessels, and wherein:
   the upper compartment of the reaction vessels have downwardly extending sidewalls that merge into an angled floor portion that defines the funnel shape, the angled floor portion declining down toward the closed bottom compartment.

4. Device according to claim 3, wherein the volume of the middle compartment is smaller compared to the upper compartment and bigger compared to the bottom compartment.

5. Device according to claim 3, wherein each compartment has an associated volume, and wherein a ratio between the volumes of the middle compartment and the upper compartment or between the volumes of the bottom compartment and the middle compartment is between 1:2 to 1:100.

6. Device according to claim 5, wherein the ratio is between about 1:5 to 1:20.

7. Device according to claim 5, wherein the ratio is about 1:10.

8. Device according to claim 2, wherein the at least one separating station and the at least one washing station cooperate with the respective at least two magnets, wherein each opposing wall of the upper compartment of the reaction vessel, constituting the funnel shape, is perpendicular to the pole axis of the magnets that are present thereat, and wherein at least two of the magnets at the separation station are configured so that each resides adjacent a respective opposing upper compartment wall of the reaction vessel at the same time.

9. Device according to claim 8, characterized in that the opposing walls of the upper compartment form together an angle different from 180° corresponding to the magnet pole that is at the angle different from 180°.

10. Device according to claim 9, wherein the angle is between about 60 and 150°.

11. Device according to claim 9, wherein the angle is between about 80 and 120°.

12. Device according to claim 2, wherein the at least one reaction vessel is a set of reaction vessels constituted by at least two vessels, said vessels being arranged symmetrically along one line.

13. Device according to claim 12, wherein the at least one pipetting device comprises:
   a first pipetting device to dispense and/or to remove part or all of the fluid from one or more of the set of reaction vessels,
   a second pipetting device to dispense and/or to remove part or all of the washing liquid from one or more of the set of reaction vessels, and a third pipetting device to dispense and/or to remove part or all of the output buffer from one or more of the set of reaction vessels.

14. Device according to claim 13, wherein the first second and third pipetting devices comprise respective tips that are held by one or more holding members, each holding member configured to hold a plurality of spaced apart tips in a defined alignment, the tips having that have opposing upper and lower free ends with the upper ends releasably attached to a respective holding member, and wherein the free ends of the tips constituting the first, the second or the third pipetting device being arranged symmetrically along one line or two lines, the two lines of each arrangement being parallel one to the other.

15. Device according to claim 14, wherein the upper and lower free ends of the tips of the first, second and third pipetting devices have the following configurations:
the tips constituting the first pipetting device being arranged symmetrically along one line,
the tips constituting the second pipetting device being arranged symmetrically along one or two lines, and
the tips constituting the third pipetting device being arranged symmetrically along two lines.

16. Device according to claim 14, wherein at least one of the first pipetting device, the second pipetting device and the third pipetting device has a different configuration from the others.

17. Device according to claim 2, wherein the upper compartment of the at least one reaction vessel includes a substantially rectangular shape with two short sides and two long sides, wherein one short side has a substantially vertically extending sidewall that is substantially aligned with a sidewall of the elongate lower compartment, and wherein the other short side has a substantially vertically extending sidewall that resides above and merges into the floor portion with the funnel shape so that the floor portion directs the fluid toward a channel associated with the elongate middle compartment.

18. Device according to claim 2, wherein the elongate middle compartment of the at least one reaction vessel has a longitudinally extending centerline that is offset from a longitudinally extending centerline of the upper compartment, and wherein the elongate middle compartment has a volume that is smaller than a volume of the upper compartment and bigger than that of the base.

* * * * *

UNITED STATES PATENT AND TRADEMARK OFFICE
CERTIFICATE OF CORRECTION

| | | |
|---|---|---|
| PATENT NO. | : 8,187,460 B2 | Page 1 of 1 |
| APPLICATION NO. | : 13/116333 | |
| DATED | : May 29, 2012 | |
| INVENTOR(S) | : Kreuwel et al. | |

It is certified that error appears in the above-identified patent and that said Letters Patent is hereby corrected as shown below:

On Title Page:
Item (75) Inventors:
    Please correct "Emiel Gerebern Maria Verwimp, Aaerendonk (BE);"
    to read -- Emiel Gerebern Maria Verwimp, Kasterlee (BE) --

Item (30) Foreign Application Priority Data: Please correct "04077153"
    to read -- 04077153.7 --

In the Patent:
Column 2, Line 2: Please correct "stray magnetic fields:"
    to read -- stray magnetic fields. --

In the Claims:
Column 19, Claim 1, Line 51: Please correct "comprises at last two magnets,"
    to read -- comprises at least two magnets, --

Column 20, Claim 2, Line 7: Please correct "comprises at last two magnets,"
    to read -- comprises at least two magnets, --

Column 21, Claim 14, Line 4: Please correct "wherein the first second"
    to read -- wherein the first, second --
    Line 8: Please correct "having that have opposing upper"
    to read -- having opposing upper --

Signed and Sealed this
Thirteenth Day of November, 2012

David J. Kappos
*Director of the United States Patent and Trademark Office*